(12) United States Patent
Hankins et al.

(10) Patent No.: US 6,447,468 B1
(45) Date of Patent: Sep. 10, 2002

(54) PORTABLE CERVICAL TRACTION APPARATUS

(76) Inventors: James T. Hankins, 212 W. Long St., Branson, MO (US) 65616; Leamon Cotton, Jr., 208 E. College St., #196, Branson, MO (US) 65616

( * ) Notice: Subject to any disclaimer, the term of this patent is extended or adjusted under 35 U.S.C. 154(b) by 0 days.

(21) Appl. No.: 09/923,488

(22) Filed: Aug. 8, 2001

(51) Int. Cl.⁷ .................................................. A61F 5/00
(52) U.S. Cl. ............................ 602/18; 602/32; 602/36; 128/845; 128/870; 128/DIG. 13
(58) Field of Search .............................. 602/18, 32, 33, 602/36; 128/845, 870

(56) References Cited

U.S. PATENT DOCUMENTS

| | | | | |
|---|---|---|---|---|
| 3,776,224 A | * | 12/1973 | McFarland | 602/18 |
| 4,250,874 A | * | 2/1981 | Rude | 602/36 |
| 4,987,886 A | | 1/1991 | McDonald et al. | |
| 5,067,483 A | | 11/1991 | Freed | |
| 5,403,266 A | | 4/1995 | Bragg et al. | |
| 5,441,479 A | * | 8/1995 | Chitwood | 602/18 |
| 5,454,781 A | * | 10/1995 | Chitwood | 602/18 |
| 5,709,649 A | | 1/1998 | Chitwood | |
| 5,752,927 A | | 5/1998 | Rogachevsky | |
| 5,823,982 A | | 10/1998 | Park | |
| 5,916,185 A | | 6/1999 | Chitwood | |
| 6,045,522 A | * | 4/2000 | Grober | 602/18 |
| 6,050,965 A | | 4/2000 | Pillai | |

* cited by examiner

Primary Examiner—Micahel A. Brown
Assistant Examiner—Fenn C Mathew
(74) Attorney, Agent, or Firm—Dale J. Ream

(57) ABSTRACT

A portable cervical traction apparatus includes a head receiving member having a U-shaped configuration and a chin strap for being secured to the back of a person's head. The head receiving member includes a protrusion for engaging the occipital bone of the person's head. The apparatus includes a base member contoured to rest atop a person's shoulders. An air cylinder is attached to the base member and includes a shaft extendable therefrom by actuation of an air pump. The shaft is coupled to the head receiving member such that the head receiving member is incrementally moved away from the base member upon actuation of the air cylinder, whereby to relieve cervical pressure or tension.

6 Claims, 6 Drawing Sheets

PORTABLE CERVICAL TRACTION APPARATUS

BACKGROUND OF THE INVENTION

This invention relates generally to traction devices and, more particularly, to a cervical traction apparatus that provides cervical tension relief without limiting the mobility of the user.

Pain in the neck and related headaches are common conditions that can often be relieved through traction therapy or proper stretching of the neck and cervical spine regions. Deterioration of cervical discs, pinched nerves, or lack of full range of motion in the neck are other problems which may be helped through traction therapy. These problems may be caused merely by sleeping in an undesirable position or from working conditions that are not ergonomically optimal.

Several devices have been proposed in the art for stretching the cervical spine area of a body. Although assumably effective for their intended purposes, devices such as those shown in U.S. Pat. Nos. 5,709,649 and 5,916,185 must be used with a patient in a recumbent position. Further, devices such as that shown in U.S. Pat. 4,987,886 are bulky and complicated and are not particularly suited for convenient and portable use by a user. Finally, devices such as the one disclosed in U.S. Pat. No. 5,403,266 are undesirable in that they surround a user's entire neck and limit normal activity during use.

Therefore, it is desirable to have a traction apparatus which may be worn and used by a user without professional assistance and without limiting normal activity. Further, it is desirable to have a traction device that is portable for convenient use anywhere. Finally, it is desirable to have a traction device that is not restrictive or constrictive relative to a user's neck.

SUMMARY OF THE INVENTION

A portable cervical traction apparatus according to the present invention includes a head receiving member having a generally U-shaped configuration and contoured to receive the back of a user's head therein. The head receiving member includes a protruded section positioned generally midway between longitudinal ends thereof, the protruded section being contoured to engage the occipital bone of a user's head when the user's head is received in the head receiving member. A chin strap connected to the ends of the head receiving member may be extended about a user's chin and tightened thereto for securely holding the head receiving member in the proper position on the user's head.

The traction apparatus further includes a base member having a generally U-shaped configuration for receiving the back of a user's neck and resting atop the user's shoulders. The base member includes a pair of padded support portions contoured to rest upon the user's shoulders and which taper downwardly and forwardly in contact with the upper chest region of the user.

A pneumatic air cylinder is mounted to the base member and includes a shaft reciprocatively mounted therein and capable of extending from a top of the air cylinder when actuated by air pressure. The shaft includes a free end pivotally coupled to the head receiving member such that the head receiving member is moved away from the base member when the air cylinder is actuated. The air cylinder is connected to a bulb-type air pump with tubing so that a user may selectably actuate the air cylinder to incrementally increase the distance between the head receiving member and base member.

The portable cervical traction apparatus is easy and convenient to place on one's shoulders and wear about one's residence. Once the head receiving member and chin strap are properly positioned, a user may pump up the air cylinder to generate a desired level of traction and then continue normal activity. A relief valve allows the traction to be released when desired.

Therefore, a general object of this invention is to provide a traction apparatus which relieves cervical tension by selectively exerting opposing pressure against a user's shoulders and occipital bone of the user's head.

Another object of this invention is to provide a traction apparatus, as aforesaid, that is selectively actuated by a user with an air cylinder and a bulb-type air pump.

Still another object of this invention is to provide a traction apparatus, as aforesaid, that is durable and aesthetically pleasing.

Yet another object of this invention is to provide a traction apparatus, as aforesaid, which is easy and convenient to operate by a user.

A further object of this invention is to provide a traction apparatus, as aforesaid, which is portable.

A still further object of this invention is to provide a traction apparatus, as aforesaid, which does not constrict about a user's neck.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
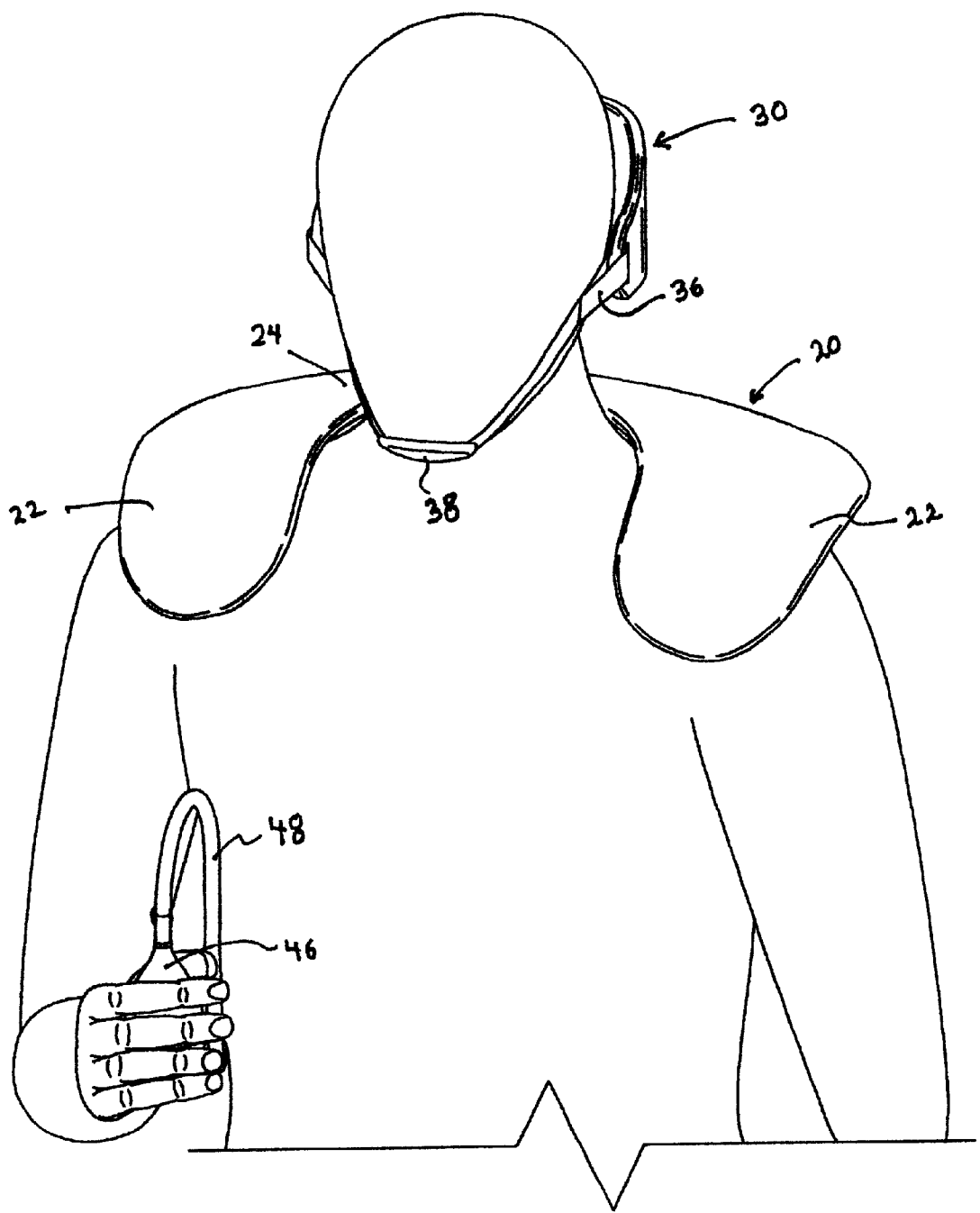
FIG. 1 is a perspective view of a portable cervical traction apparatus in use by a user according to one embodiment of the present invention.

A portable cervical traction apparatus according to the present invention will now be described with reference to FIGS. 1 through 6 of the accompanying drawings. A traction apparatus 10 according to one embodiment of the invention includes a base member 20 coupled to a head receiving member 30 and adapted to rest upon a user's shoulders and to be strapped to the user's head, respectively (FIG. 1). The base member 20 includes a pair of support portions 22 and a neck receiving portion 24 intermediate the support portions 22. Preferably, the base member 20 is integrally constructed with a generally U-shaped configuration such that a user's neck may be received within the U-shaped cutout so as to bear against the neck receiving portion 24

Figure 2:
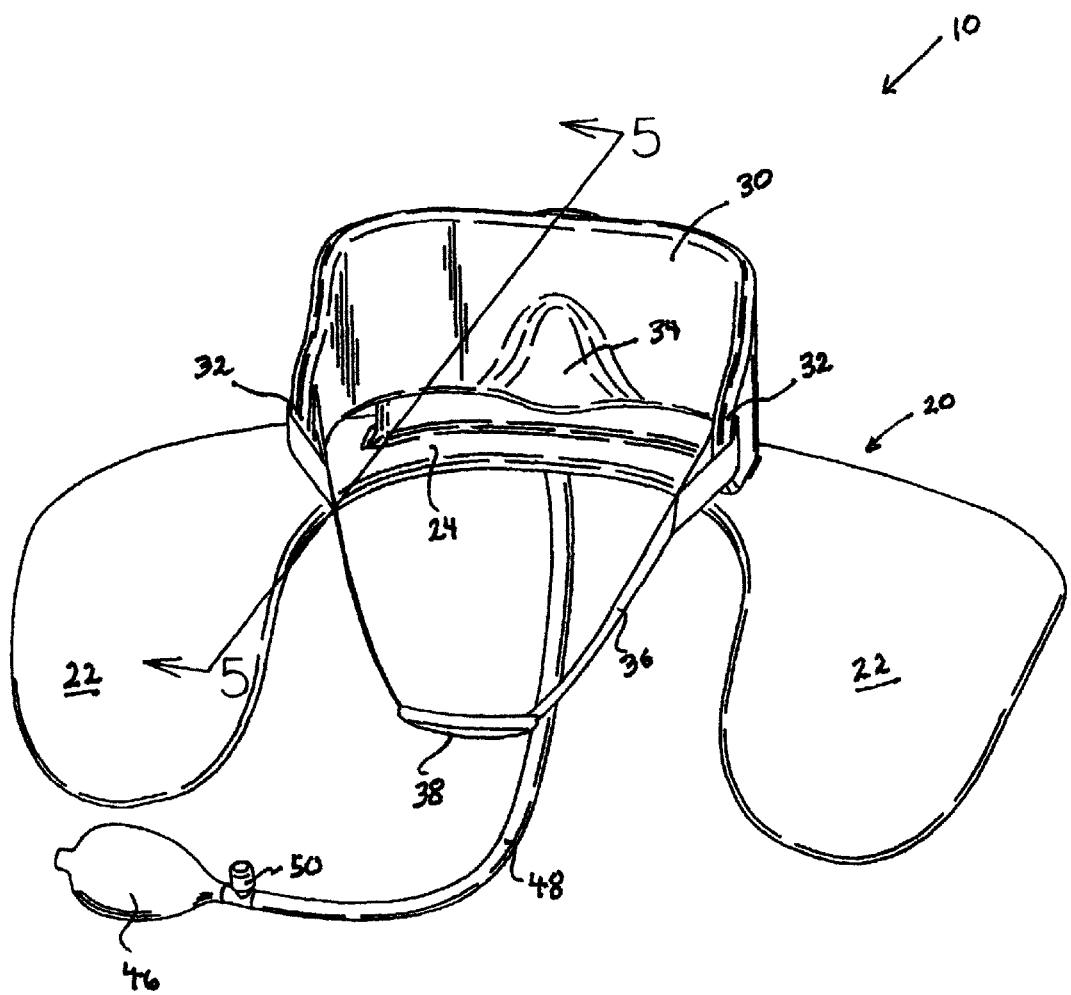
FIG. 2 is a perspective view of the apparatus as in FIG. 1 with the apparatus removed from the user's body.

(FIG. 2). The support portions 22 extend forwardly and are contoured to gradually taper downwardly so as to rest upon both a user's shoulders and upper chest region (FIG. 1). Preferably, the base member 20 is constructed of molded plastic and includes a resilient pad 26 on a bottom side thereof (FIG. 3), the pad preferably being constructed of foam or urethane.

The head receiving member 30 includes a generally U-shaped construction that would be generally rectangular if flattened. The head receiving member 30 includes opposed ends 32 and is contoured to receive the back of a person's head against the inner surface thereof with the opposed ends 32 being positioned just behind each of a person's ears (FIG. 1). The head receiving member 30 includes an inwardly protruded section 34 contoured to engage and bear against the occipital bone of the back of a person's head when the head receiving member 30 is attached to the person's head.

A chin strap 36 is coupled to respective ends 32 of the head receiving member 30 (FIG. 2). Preferably, ends of the chin strap 36 extend through slots defined by each opposed end 32 in a conventional manner although other attachments or fasteners would also be suitable, such as snaps, buttons, rivets, or the like. The chin strap 36 is constructed of a nylon material although an elastic material may alternatively be used. A chin support 38 constructed of a soft leather material is attached to the chin strap 36 for actually supporting a person's chin and this may include a buckle or the like.

Figure 3:
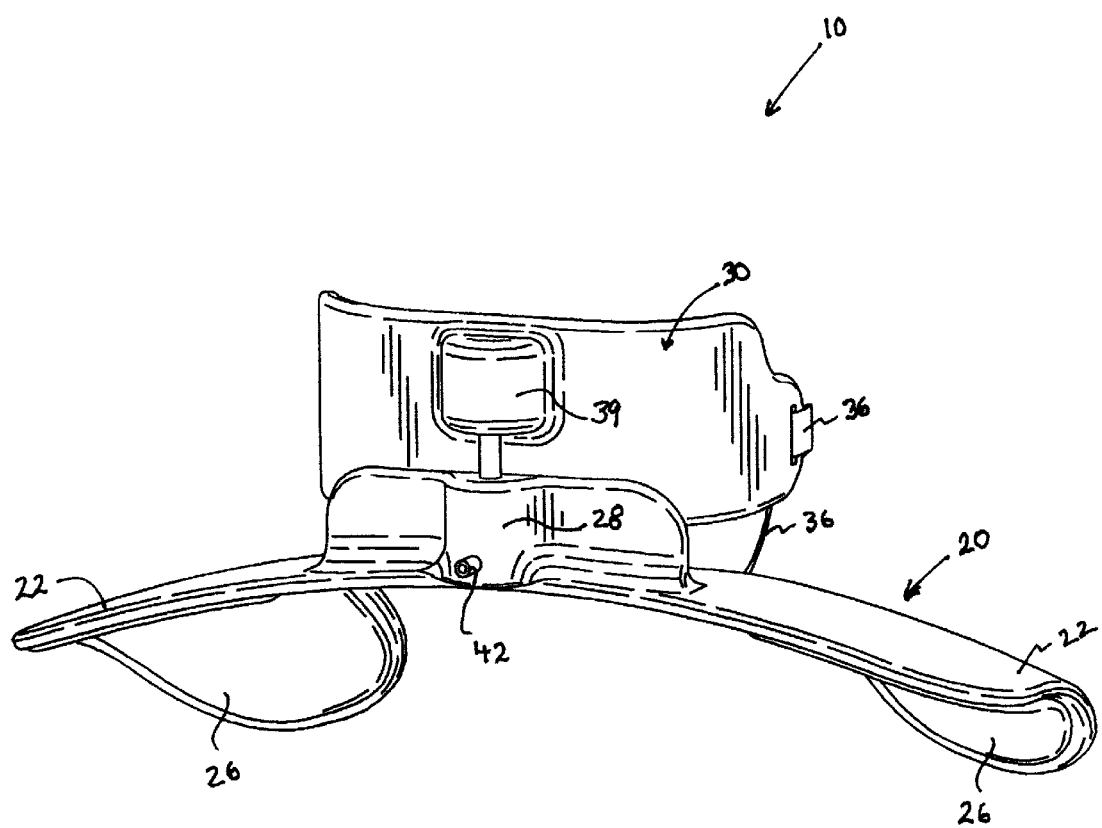
FIG. 3 is a rear perspective view of the apparatus as in FIG. 2.
Figure 4:
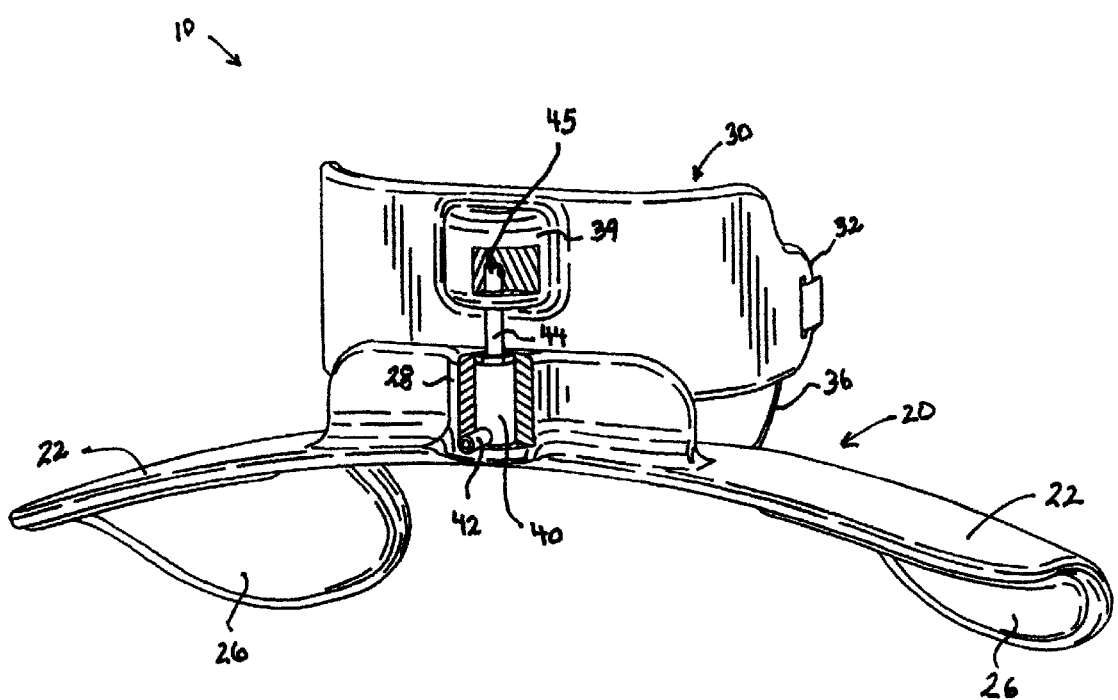
FIG. 4 is a rear perspective view of the apparatus as in FIG. 3 with portions of the air cylinder chamber cut away.
Figure 5:
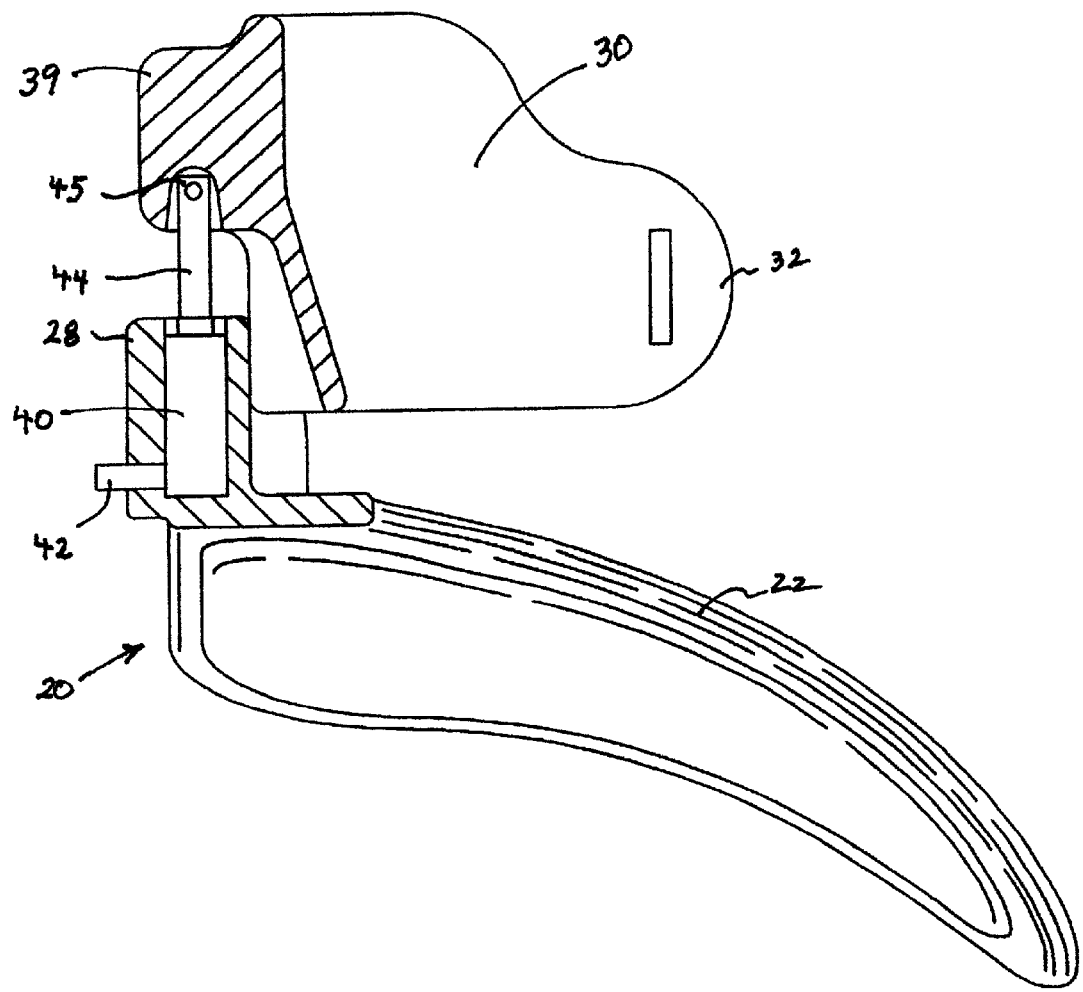
FIG. 5 is a sectional view of the apparatus taken along line 5—5 of FIG. 2.

A pneumatic air cylinder 30 is fixedly attached to the neck receiving portion 24 of the base member 20 (FIG. 4). The base member 20 integrally includes a housing 28 in which the air cylinder is positioned (FIG. 3). A nozzle 42 is connected to the air cylinder 30 and extends through the housing 28. A shaft 44 is reciprocatively mounted in the air cylinder 30 for extension or retraction through a top thereof. A free end 45 of the shaft 44 is pivotally coupled to a rear portion 39 of the head receiving member 30 (FIGS. 4 and 5). The pivotal coupling allows the entire head receiving member 30 to pivot forward or backward in conjunction with a user's desired neck movement. The air cylinder 30 is connected to a bulb-type air pump 46 with tubing 48, the shaft 44 being incrementally extended by increased air pressure as air is manually pumped into the air cylinder 30 by a user squeezing the bulb. Therefore, the head receiving member 30 is moved away from the base member 20 as the shaft 44 extends from the air cylinder 30. A relief valve 50 is positioned along the tubing 48 for selectively releasing air from the air cylinder 30 such that a user may adjust the amount of traction or release the traction completely.

In use, a user may position the base member 20 atop his shoulders such that the back of his neck is received against the neck receiving portion 24 and the support portions 22 rest upon his shoulders and upper chest region (FIG. 1). Having positioned the base member 20, the head receiving member 30 will already be generally positioned to receive the user's head. By pumping the air pump 46 or by releasing air through the relief valve 50, the head receiving member 30 may be perfectly positioned such that the occipital bone of the user's head engages the protruded section 34 of the head receiving member 30. The user may then extend the chin strap 36 about his chin and tighten it accordingly. Finally, the air pump 46 may be repeatedly squeezed to inject air into the air cylinder 30 and correspondingly extend the shaft 44 therefrom. This extension moves the head receiving member 30 upward and away from the base member 20 so as to increase the cervical traction to a desired level. With the traction apparatus 10 properly adjusted, the user may participate in routine activity. When desired, the user may actuate the relief valve 50 to release air from the air cylinder 30 which retracts the shaft 44 and returns the head receiving member 30 to its initial position.

Figure 6:
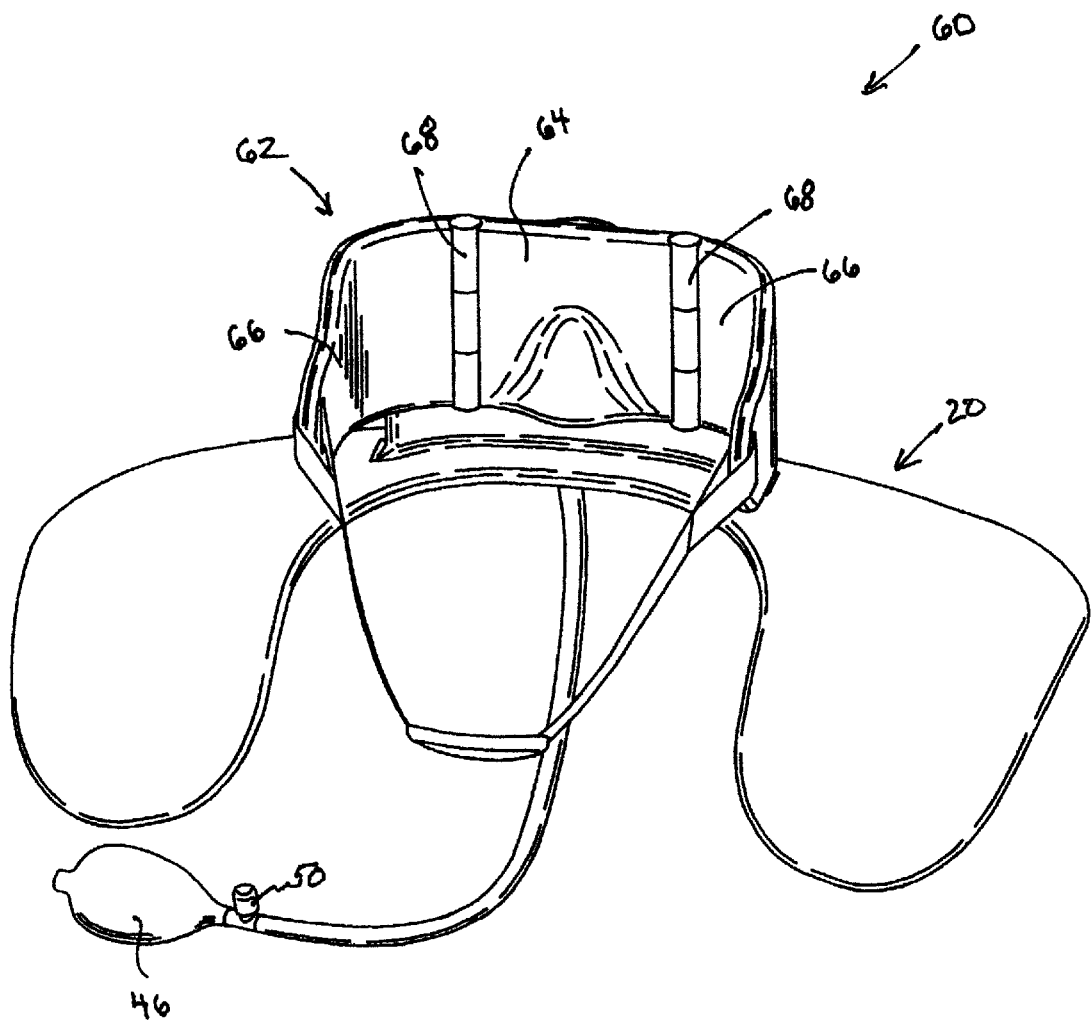
FIG. 6 is a perspective view of a portable cervical traction apparatus according to another embodiment of the present invention.
Figure 1:
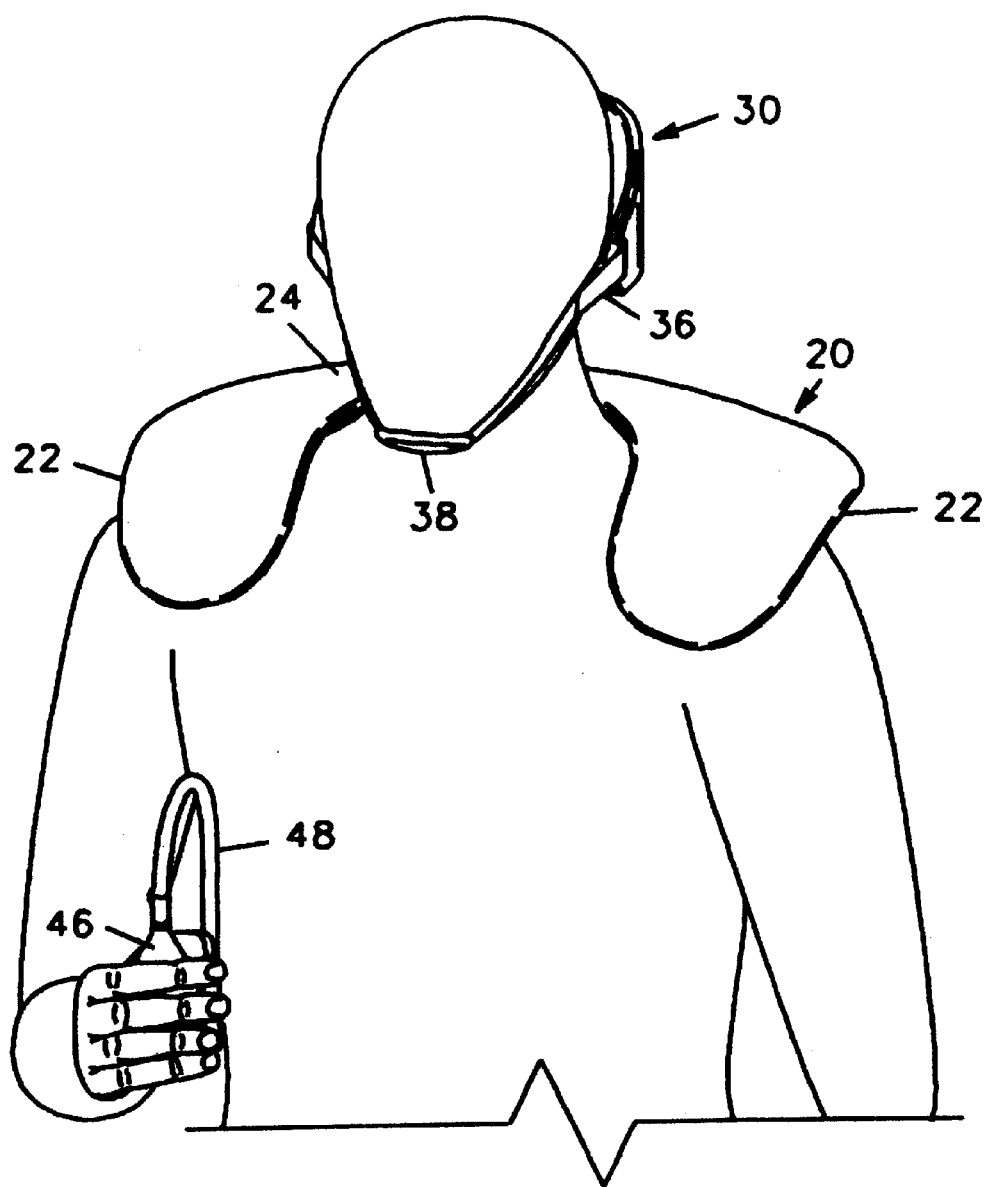
Figure 2:
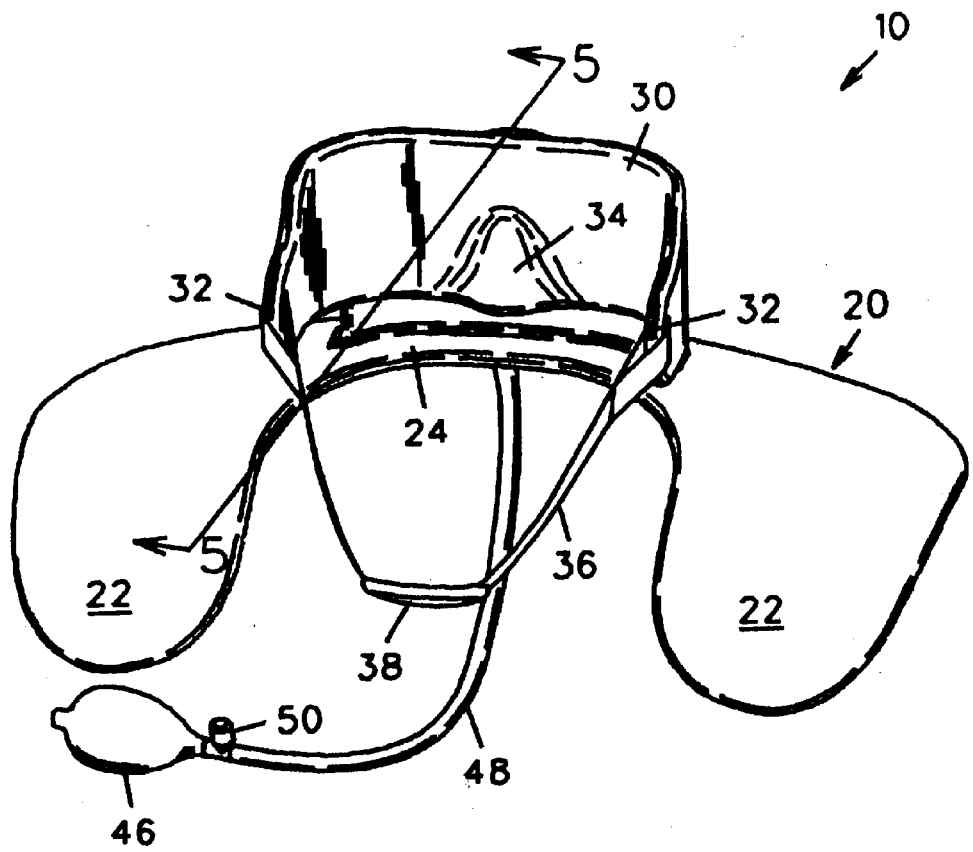
Figure 3:
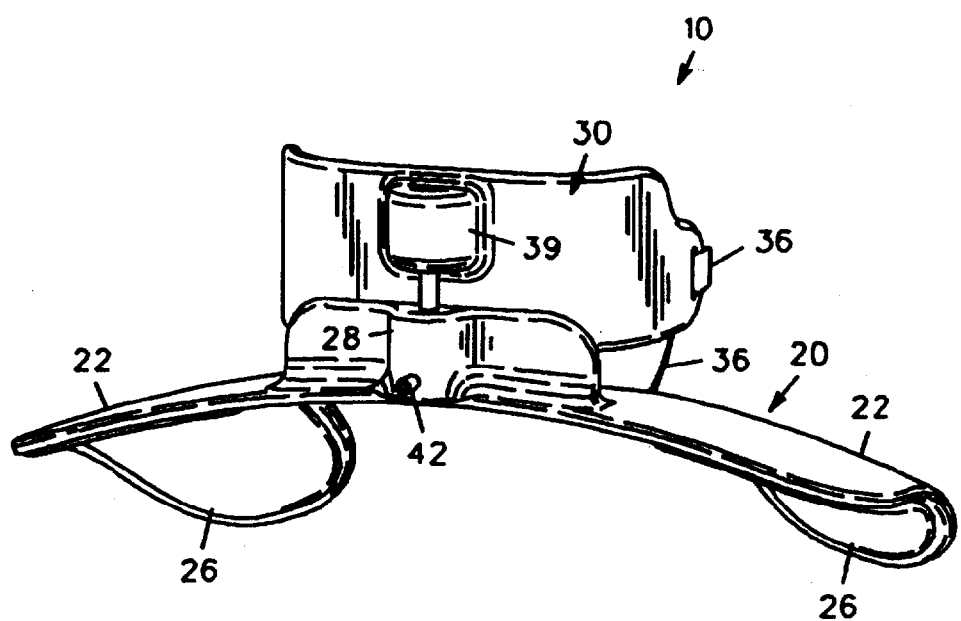
Figure 4:
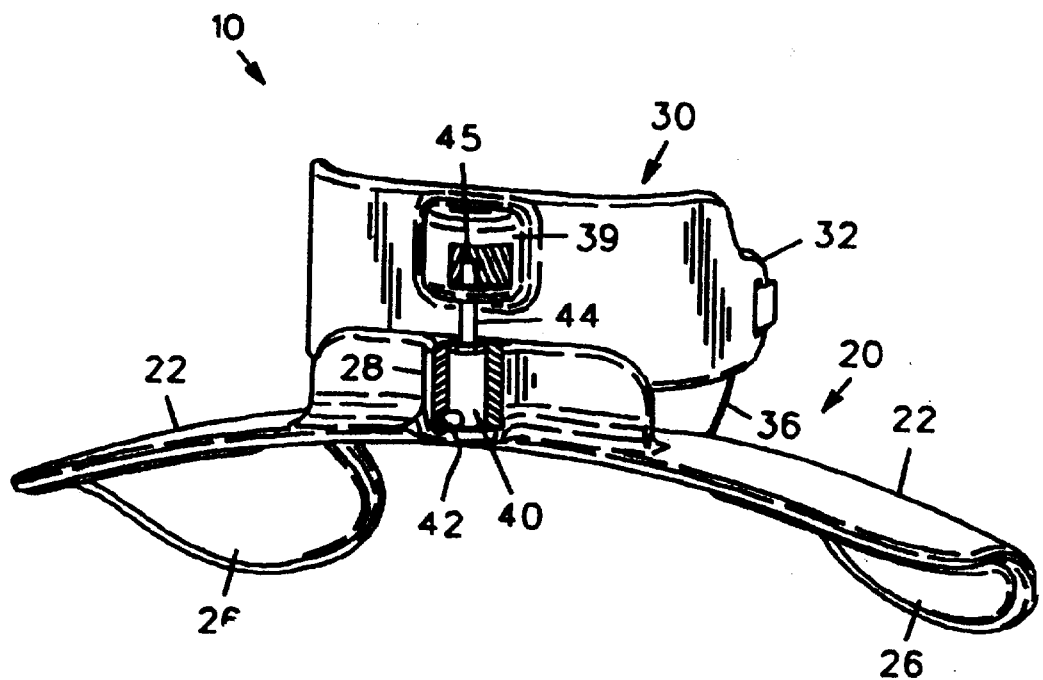
Figure 5:
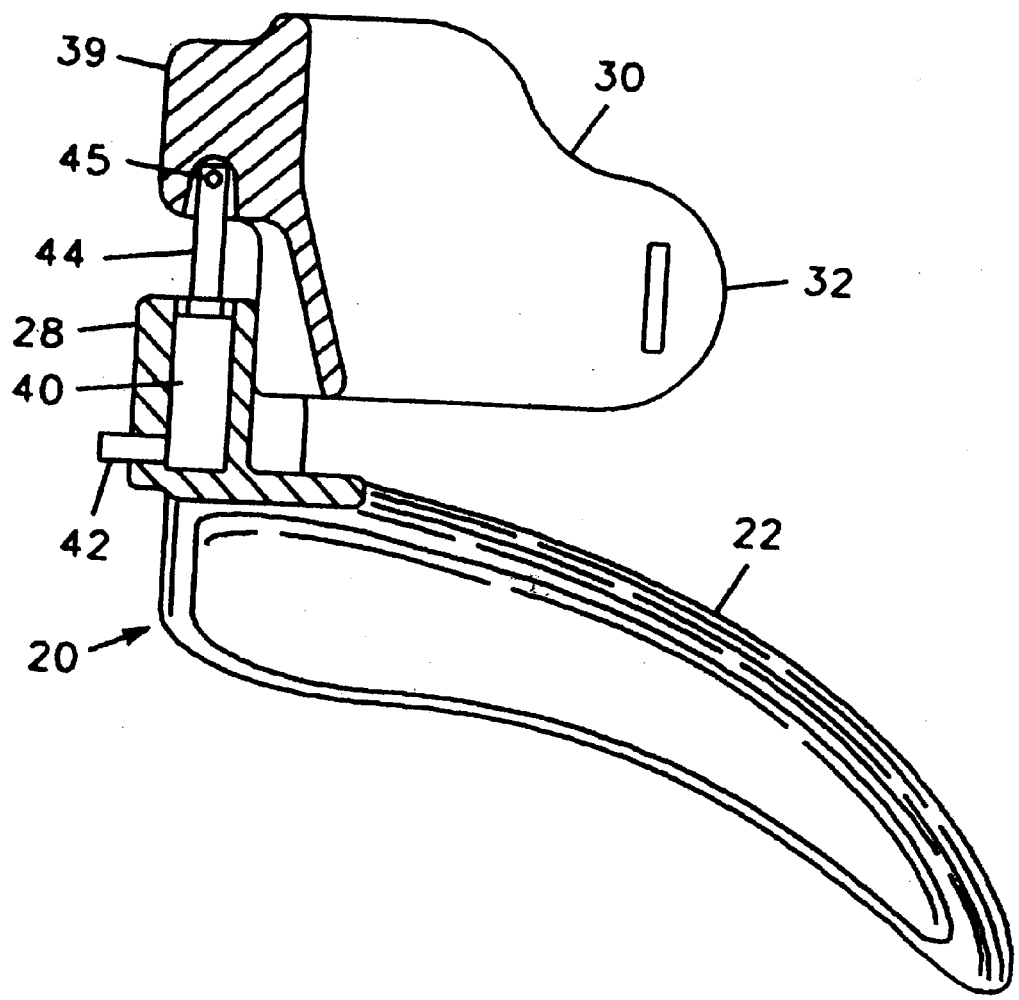
Figure 6:
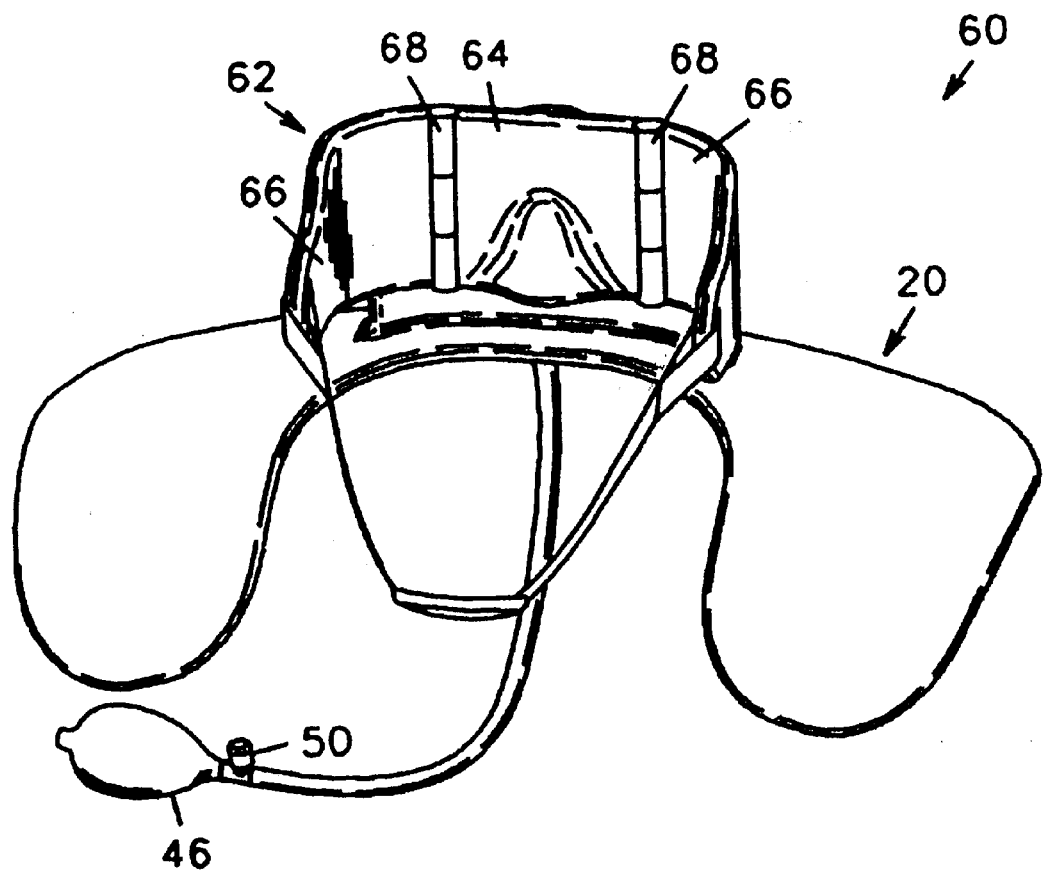

A portable cervical traction apparatus 60 according to another embodiment of this invention is shown in FIG. 6 and is substantially similar to the embodiment described above except as specifically noted below. In this embodiment, the head receiving member 62 is divided into three portions. A back panel 64 is positioned intermediate a pair of side panels 66, the side panels being pivotally coupled to opposing edges of the back panel 64 with respective spring hinges 68. The side panels 66 are normally biased such that the head receiving member 62 has a generally U-shaped configuration. However, the side panels 66 may be pivoted outwardly to correspond to the width of a person's head that is being received by the head receiving member 62.

In another embodiment (not shown), the free end of the shaft 44 of the air cylinder 30 is fixedly attached to the rear portion 39 of the head receiving member 30 such that forward or backward movement thereof is precluded.

It is understood that while certain forms of this invention have been illustrated and described, it is not limited thereto except insofar as such limitations are included in the following claims and allowable functional equivalents thereof.

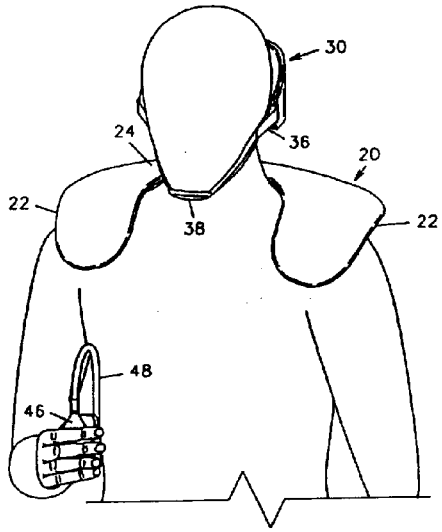

Having thus described the invention, what is claimed as new and desired to be secured by Letters Patent is as follows:

1. A portable cervical traction apparatus, comprising:
   a head receiving member having a generally U-shaped configuration for receiving the back of a person's head and having opposed ends adapted to be positioned behind a person's ears, said head receiving member having a protruded section adapted to engage and bear against the occipital bone of the person's head;
   a chin strap attached to said opposed ends of said head receiving member and adapted to extend about a person's chin for selectively securing said head receiving member to the person's head;
   a base member having a neck receiving portion contoured to receive the back of a person's neck and a pair of support portions connected to opposed ends of said neck receiving portion adapted to rest atop a person's shoulders, said base member having a generally U-shaped configuration with said support portions being tapered to rest partially upon the upper chest of a person;
   an air cylinder fixedly attached to said base member and having a shaft reciprocatively positioned therein for selectable extension therefrom, said shaft having a free end pivotally coupled to said head receiving member such that said head receiving member is selectively movable in forward and rearward directions; and
   an air pump connected by tubing to said air cylinder for incrementally pumping air into said air cylinder so as to selectably extend said shaft, whereby extension of said shaft causes said head receiving member to move away from said base member.

2. The apparatus as in claim 1, wherein said tubing includes a relief valve therein for selectably releasing air from said air cylinder.

3. The apparatus as in claim 1 wherein said air pump is a bulb-type air pump for incrementally pumping air into said air cylinder by squeezing said bulb-type air pump.

4. The apparatus as in claim 1 wherein said base member includes a resilient pad attached to a bottom surface thereof.

5. The apparatus as in claim 1 wherein said head receiving member comprises a back panel and a pair of side panels pivotally connected to opposed edges of said back panel, said side panels being inwardly biased and outwardly pivotal upon contact with the head of a person being received by said head receiving member.

6. A portable cervical traction apparatus, comprising:
- a head receiving member having a generally U-shaped configuration for receiving the back of a person's head and having opposed ends adapted to be positioned behind a person's ears, said head receiving member having a protruded section adapted to engage and bear against the occipital bone of the person's head;
- a chin strap attached to said opposed ends of said head receiving member and adapted to extend about a person's chin for selectively securing said head receiving member to the person's head;
- a base member having a neck receiving portion contoured to receive the back of a person's neck and a pair of support portions connected to opposed ends of said neck receiving portion adapted to rest atop a person's shoulders, said base member having a generally U-shaped configuration with said support portions being tapered to rest partially upon the upper chest of a person, said base member having a resilient pad attached to a bottom surface thereof;
- an air cylinder fixedly attached to said base member and having a shaft reciprocatively positioned therein for selectable extension therefrom, said shaft having a free end pivotally coupled to said head receiving member such that said head receiving member is selectively movable in forward and rearward directions;
- an air pump connected by tubing to said air cylinder for incrementally pumping air into said air cylinder so as to selectably extend said shaft, whereby extension of said shaft causes said head receiving member to move away from said base member;
- a relief valve connected to said tubing for selectably releasing air from said air cylinder; and
- wherein said head receiving member comprises a back panel and a pair of side panels pivotally connected to opposed edges of said back panel with spring hinges, said side panels being inwardly biased and outwardly pivotal upon contact with the head of a person being received by said head receiving member.

\* \* \* \* \*

UNITED STATES PATENT AND TRADEMARK OFFICE
CERTIFICATE OF CORRECTION

PATENT NO.    : 6,447,468 B1
DATED         : September 10, 2002
INVENTOR(S)   : Hankins et al.

It is certified that error appears in the above-identified patent and that said Letters Patent is hereby corrected as shown below:

Please delete title page and substitute attached title page.

Drawings,
Please delete drawings Figs. 1-6, and replace with the attached formal drawings, Figs 1-6.

Signed and Sealed this

Fifteenth Day of April, 2003

JAMES E. ROGAN
*Director of the United States Patent and Trademark Office*

United States Patent
Hankins et al.

(10) Patent No.: US 6,447,468 B1
(45) Date of Patent: Sep. 10, 2002

(54) PORTABLE CERVICAL TRACTION APPARATUS

(76) Inventors: James T. Hankins, 212 W. Long St., Branson, MO (US) 65616; Leamon Cotton, Jr., 208 E. College St., #196, Branson, MO (US) 65616

(*) Notice: Subject to any disclaimer, the term of this patent is extended or adjusted under 35 U.S.C. 154(b) by 0 days.

(21) Appl. No.: 09/923,488

(22) Filed: Aug. 8, 2001

(51) Int. Cl.$^7$ ................................................ A61F 5/00
(52) U.S. Cl. ....................... 602/18; 602/32; 602/36; 128/845; 128/870; 128/DIG. 13
(58) Field of Search .................. 602/18, 32, 33, 602/36; 128/845, 870

(56) References Cited

U.S. PATENT DOCUMENTS

| | | | |
|---|---|---|---|
| 3,776,224 A | * 12/1973 | McFarland | 602/18 |
| 4,250,874 A | * 2/1981 | Rude | 602/36 |
| 4,987,886 A | 1/1991 | McDonald et al. | |
| 5,067,483 A | 11/1991 | Freed | |
| 5,403,266 A | 4/1995 | Bragg et al. | |
| 5,441,479 A | * 8/1995 | Chitwood | 602/18 |
| 5,454,781 A | * 10/1995 | Chitwood | 602/18 |
| 5,709,649 A | 1/1998 | Chitwood | |
| 5,752,927 A | 5/1998 | Rogachevsky | |
| 5,823,982 A | 10/1998 | Park | |
| 5,916,185 A | 6/1999 | Chitwood | |
| 6,045,522 A | * 4/2000 | Grober | 602/18 |
| 6,050,965 A | 4/2000 | Pillai | |

* cited by examiner

Primary Examiner—Micahel A. Brown
Assistant Examiner—Fenn C Mathew
(74) Attorney, Agent, or Firm—Dale J. Ream

(57) ABSTRACT

A portable cervical traction apparatus includes a head receiving member having a U-shaped configuration and a chin strap for being secured to the back of a person's head. The head receiving member includes a protrusion for engaging the occipital bone of the person's head. The apparatus includes a base member contoured to rest atop a person's shoulders. An air cylinder is attached to the base member and includes a shaft extendable therefrom by actuation of an air pump. The shaft is coupled to the head receiving member such that the head receiving member is incrementally moved away from the base member upon actuation of the air cylinder, whereby to relieve cervical pressure or tension.

6 Claims, 6 Drawing Sheets